United States Patent [19]

Gomez Parra et al.

[11] Patent Number: 4,563,528

[45] Date of Patent: Jan. 7, 1986

[54] PROCESS FOR PREPARING 5 PYRIDYL PYRIDINE-2 (1H)-ONES

[75] Inventors: Vicente Gomez Parra; Pedro Gonzalez Hernandez; Félix Sanchez Alonso; Tomás Torres Cebada, all of Madrid, Spain

[73] Assignee: Fabrica De Productos Quimicos Y Farmaceuticos Abello, S.A., Madrid, Spain

[21] Appl. No.: 601,898

[22] Filed: Apr. 19, 1984

[51] Int. Cl.[4] .............................................. C07D 401/04
[52] U.S. Cl. .................................... 546/261; 546/297; 546/264; 546/288
[58] Field of Search ................ 546/261, 264, 291, 288

[56] References Cited

U.S. PATENT DOCUMENTS 4,107,315  8/1978  Lesher et al. ........................ 424/263

*Primary Examiner*—Alan L. Rotman
*Attorney, Agent, or Firm*—William H. Nicholson; Michael C. Sudol

[57] ABSTRACT

5-Pyridinyl-6-$R_2$-3-$R_1$-2(1H)-pyridinones (I), where $R_2$ is hydrogen or lower alkyl and $R_1$ is a cyano, a carbamoyl or an amino group are prepared: by reaction of 1-$R_2$-1-oxo-2-pyridinyl-3-dialkylaminopropane (II) with malonamide under solid-liquid or liquid-liquid phase transfer catalysis conditions to obtain 1,2-dihydro-2-oxo-6-$R_2$-5-pyridinylnicotinamide (IV), or by reaction of II with cyanoacetamide under solid-liquid or liquid-liquid phase transfer catalysis conditions to obtain 1,2-dihydro-2-oxo-6-$R_2$-5-pyridinylnicotinonitrile (III) and partially hydrolizing III to yield IV; finally the carbamoyl group of IV is converted to amino and 1,2-dihydro-2-oxo-6-$R_2$-5-pyridinyl-3-aminopyridin-2-one are obtained.

1 Claim, No Drawings

PROCESS FOR PREPARING 5 PYRIDYL PYRIDINE-2 (1H)-ONES

BACKGROUND OF THE INVENTION (A) Field of the Invention

This invention is related to an improved preparation of 5-pyridinyl-6-$R_2$-3-$R_1$-2(1H)pyridinones and to intermediates used therein.

(B) Description of the Prior Art

Some of compounds I, IV and V are described as cardiotonically active drugs (U.S. Pat. No. 4,107,315; Ger. Offen. No. 3944568, etc.) and was prepared by condensating under classical conditions, preferred by employing sodium methoxide in methanol or dimethylformamide with only low to moderate yields and in a drastic basic media.

The present specification relates to a novel process for preparing 5-pyridyl pyridine-2(1H)-ones of general formula I

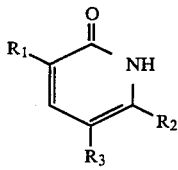

in which $R_1$ is an amino group, $R_2$ a hydrogen atom or a lower alkyl group and $R_3$ is a 4-, 3- or 2-pyridyl group as well as the intermediates used in its preparation.

Some of the compounds referred to this invention have shown to be effective as antidysrhythmic agents, and also some of them are useful intermediates in the preparation of other derivatives with the therapeutic activity mentioned.

According to this invention the compounds of general formula I are prepared through several steps from the pyridyl derivatives of general formula II as it is depicted in the next scheme:

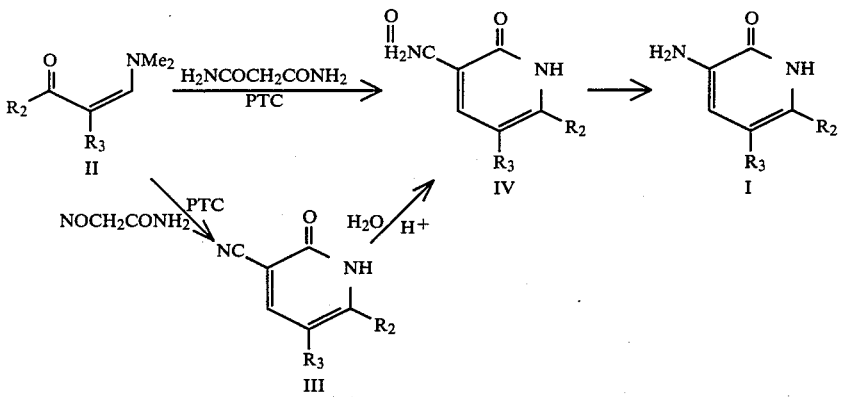

The first step comprises reacting a compound of general formula II, where $R_2$ and $R_3$ have the meanings given above, with an excess of malonamide, both dissolved in a suitable solvent, such as chloroform, methylene chloride, acetonitrile, dimethylformamide, etc., in the presence of a molar excess of a finely ground alkali metal, alkaline-earth metal carbonate, bicarbonate or hydroxide and a quaternary ammonium or phosphonium salt which performs as a phase-transfer catalyst (PTC). This process may be suitably conducted at a temperature within the range of about 20° to 160° C., continuously stirred at a rate higher than 200 r.p.m. and for a period within the range of about 24 to 72 hours to afford compounds of general formula IV which can be purified by recrystallization from a suitable solvent, although this is not necessary for them to be used in the next step.

The compounds of general formula IV can also be prepared by treatment of a compound of general formula II, where $R_2$ and $R_3$ have the meanings given above, with cyanoacetamide in a suitable solvent such as chloroform, methylene chloride, acetonitrile, dimethylformamide, etc., in the presence of a molar excess of a finely ground alkali metal, alkaline-earth metal carbonate, bicarbonate or hydroxide and a quaternary ammonium or phosphonium sal which performs as a phase-transfer catalyst. This process may be suitably conducted at a temperature within the range of about 10° to 160° C., continuously stirred at a rate higher than 200 r.p.m. and for a period within the range of about 2 to 36 hours to afford 3-cyano-pyridine-2(1H)-ones of general formula III, where $R_2$ and $R_3$ have the meanings given above. These compounds can be purified by recrystallization from a suitable solvent, although this is not necessary to carry on with the synthesis. In a second step, the cyano group of this compounds is partially hydrolyzed to a carbamoyl group following the usual procedures to afford the derivatives of general formula IV, where $R_2$ and $R_3$ have the meanings given above.

In the second step of the reaction the carboxamide of general formula IV leads to the corresponding primary amine following the usual procedures, for example by treatment with an alkaline hypohalide [Org. React., 3, 267(1946)], by the action of hydrazine and further nitrosation and heat [Org. React., 3, 337(1946)], etc., affording the title derivatives of general formula I which are purified by crystallization from a suitable solvent.

The following examples ilustrate the processes used for preparing the 5-pyridyl pyridine-2(1H)-ones, and are not intended to limit the scope of this invention.

EXAMPLE 1

5-(4-pyridyl)-3-carbamoyl-pyridine-2(1H)-one

Into a 2-liter round-bottomed flask, provided with a mechanical stirrer, a reflux condenser and a calcium chloride tube, 2.5 L of acetonitrile, 100 g of 2-(4-pyridyl)-3-dimethylacroleine, 64 g of malonamide, 20 g of tetrabutylammonium bromide and 300 g of finely ground potassium carbonate are placed. The mixture is vigorously stirred at 400 to 600 r.p.m. and refluxed for 24 hours. Then 50 g of finely ground potassium hydroxide are added and stirring and refluxing continued for 4 hours more. The reaction mixture was evaporated to dryness "in vacuo", then 2 L of water are added and the mixture is distilled under reduce pressure affording a first fraction which contains the excess of acetonitrile, thus reducing the total mixture volume to approximately 2 L. This solution is kept at about 40° to 60° C. and 50% sulphuric acid is added until pH=7 whereupon a pale beige product precipitates. The precipitate is filtered under "vacuum", washed with water and dried in the air to yield 72 g (58%) of the title compound. M.p.>300° C. Following a similar process and starting from suitable products of general formula II the following products, among others, are prepared:

5-(3-Pyridyl)-3-carbamoyl-pyridine-2(1H)-one

Yield 68%. M.p.>300° C.

5-(4-Pyridyl)-3-carbamoyl-6-methyl-pyridine-2(1H)-one

Yield 62%. M.p.>300° C.

EXAMPLE 2

5-(4-pyridyl)-3-cyano pyridine-2(1H)-one

Into a 3-liter round bottomed flask provided with a mechanical stirrer and a calcium chloride tube, 2.5 L of 2-(4-pyridyl)-3-dimethylacroleine, 52.5 g of cyanoacetamide, 20 g of tetrabutylammonium bromide and 100 g of finely ground potassium hydroxide are added. The mixture is vigorously stirred at 400 to 600 r.p.m. at room temperature (water bath 20° C.) for 4 hours. Then the reaction mixture is evaporated to dryness "in vacuo" and 2 L of water are added and distilled under reduced pressure to afford a first fraction distillation in which the excess of acetonitrile is contained to end up with a volume of approximately 2 L. The solution is kept at a temperature between 40° to 60° C. and 50% sulphuric acid is added until pH=7 whereupon a yellow solid product precipitates. This precipitate filtered under "vacuum", washed with water and dried in the air to afford 95 g (85%) of the title compound. M.p.>300° C. Following a similar procedure and starting from suitable products of general formula II the following compounds, among others, are prepared:

5-(2-pyridyl)-3-cyano-pyridine-2(1H)-one

Yield 90%. M.p.>300° C.

5-(4-pyridyl)-3-cyano-6-methyl-pyridine-2(1H)-one

Yield 82%. M.p.>300° C.

5-(3-Pyridyl)-3-cyano pyridine-2(1H)-one

Yield 87%. M.p.>300° C.

5-(3-pyridyl)-3-cyano-6-ethyl-pyridine-2(1H)-one

Yield 68%. M.p.>300° C.

We claim:
1. In a process for the preparation of a compound of formula

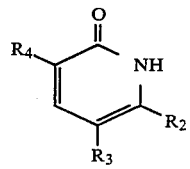

wherein $R_4$ is —CN or —CONH$_2$, $R_2$ is a hydrogen atom or a lower alkyl group and $R_3$ is a 4-, 3- or 2-pyridyl group which comprises: treating a compound of formula

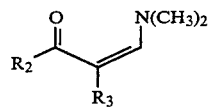

with an excess of a compound of formula: $R_4$—CH$_2$CONH$_2$ wherein the improvement comprises using a molar excess of a finely ground alkaline or alkaline earth carbonate, bicarbonate or hydroxide and tetrabutylammonium bromide at 10°–160° C. while stirring at a rate higher than 200 r.p.m.

* * * * *